(12) United States Patent
Simon et al.

(10) Patent No.: US 9,394,781 B2
(45) Date of Patent: *Jul. 19, 2016

(54) LOGGING-WHILE-DRILLING TOOL INCORPORATING ELECTRONIC RADIATION GENERATOR AND METHOD FOR USING SAME

(71) Applicant: Schlumberger Technology Corporation, Sugar Land, TX (US)

(72) Inventors: Matthieu Simon, Houston, TX (US); Peter Wraight, Skillman, NJ (US); Christian Stoller, Princeton Junction, NJ (US); Kenneth E. Stephenson, Plainsboro, NJ (US); Andrew Bazarko, Princeton, NJ (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/281,945

(22) Filed: May 20, 2014

(65) Prior Publication Data

US 2014/0251690 A1    Sep. 11, 2014

Related U.S. Application Data

(63) Continuation of application No. 12/959,485, filed on Dec. 3, 2010, now Pat. No. 8,742,328.

(51) Int. Cl.
*G01V 5/12* (2006.01)
*E21B 47/00* (2012.01)
(Continued)

(52) U.S. Cl.
CPC . *E21B 47/00* (2013.01); *G01V 5/04* (2013.01); *G01V 5/12* (2013.01); *G01V 5/125* (2013.01); *G01N 23/083* (2013.01)

(58) Field of Classification Search
CPC ........ G01V 5/125; G01V 5/12; G01N 23/083
See application file for complete search history.

(56) References Cited

U.S. PATENT DOCUMENTS

| 4,048,495 A | 9/1977 | Ellis |
| 4,698,501 A | 10/1987 | Paske |

(Continued)

FOREIGN PATENT DOCUMENTS

| CN | 1864081 A | 11/2006 |
| CN | 101451434 A | 6/2009 |
| WO | 2012074834 A1 | 6/2012 |

OTHER PUBLICATIONS

Notification of the First Office Action and Search Report for Chinese Patent Application No. 20110064463.9 dated Apr. 29, 2015.

(Continued)

*Primary Examiner* — Marcus Taningco
(74) *Attorney, Agent, or Firm* — Michael Dae

(57) ABSTRACT

Logging-while-drilling tools incorporating an electronic radiation generator, such as an electronic X-ray generator, and a method for using the same are provided. One example of such a logging-while-drilling tool may include a circumferential drill collar, a chassis disposed radially interior to the drill collar, and an electronic X-ray generator and an X-ray detector disposed within the chassis. The electronic X-ray generator may emit X-rays out of the logging-while-drilling tool into a subterranean formation. The X-ray detector may detect X-rays that return to the logging-while-drilling tool after scattering in the subterranean formation, which may be used to determine a density and/or a lithology of the subterranean formation.

9 Claims, 16 Drawing Sheets

(51) Int. Cl.
*G01V 5/04* (2006.01)
*G01N 23/083* (2006.01)

(56) References Cited

U.S. PATENT DOCUMENTS

| | | | |
|---|---|---|---|
| 4,894,534 A | 1/1990 | Paske et al. | |
| 5,627,368 A | 5/1997 | Moake | |
| 5,804,820 A | 9/1998 | Evans et al. | |
| 5,841,135 A | 11/1998 | Stoller et al. | |
| 6,944,548 B2 | 9/2005 | Radtke et al. | |
| 7,073,378 B2 | 7/2006 | Smits et al. | |
| 7,564,948 B2 | 7/2009 | Wraight et al. | |
| 7,668,293 B2 | 2/2010 | Wraight et al. | |
| 7,817,781 B2 | 10/2010 | Wraight et al. | |
| 7,960,687 B1 | 6/2011 | Simon et al. | |
| 8,742,328 B2 | 6/2014 | Simon et al. | |
| 2002/0038849 A1 | 4/2002 | Adolph et al. | |
| 2005/0028586 A1 | 2/2005 | Smits et al. | |
| 2007/0119243 A1 | 5/2007 | Smits et al. | |
| 2009/0147907 A1 | 6/2009 | Wraight | |
| 2009/0274276 A1 | 11/2009 | Wraight et al. | |
| 2012/0138782 A1 | 6/2012 | Simon et al. | |

OTHER PUBLICATIONS

D. Ellis & J. Signer, "Well Logging for Earth Scientists," 2nd Ed., Ch. 12, pp. 289-324, Springer (2007).

European Search Report issued in related EP application 11844569.1 on Apr. 21, 2016, 8 pages.

LOGGING-WHILE-DRILLING TOOL INCORPORATING ELECTRONIC RADIATION GENERATOR AND METHOD FOR USING SAME

CROSS-REFERENCE TO RELATED APPLICATIONS

This application is a continuation of co-pending U.S. patent application Ser. No. 12/959,485, filed Dec. 3, 2010, which is herein incorporated by reference.

BACKGROUND

The present disclosure relates generally to techniques for logging-while-drilling (LWD) and, more particularly, to techniques for determining formation properties using an LWD tool incorporating an electronic radiation generator, such as an electronic X-ray generator.

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Measurement of the bulk density and/or lithology of a subterranean formation are essential to programs for downhole logging, whether wireline or logging-while-drilling (LWD). Conventionally, many downhole well-logging tools use emissions of radiation, such as gamma-rays, to determine a property of a subterranean formation such as lithology or density. Once emitted into the formation, the gamma-rays may interact with the formation through Compton scattering, which may attenuate the gamma-rays, and/or the photoelectric effect, through which elements of the formation may absorb the gamma-rays. The degree to which the formation causes the gamma-rays to be Compton scattered and/or to be absorbed via the photoelectric effect may depend respectively on the density and lithology of the formation. That is, formations of various densities and lithologies will cause Compton scattering and absorption via the photoelectric effect in a predictable manner. Thus, by detecting the spectrum and the number of gamma-rays that return to the downhole tool, the density and/or lithology of the formation may be determined.

Conventionally, the formation bulk density measurement has relied on discrete energy radioisotopic gamma-ray sources, predominately $^{137}Cs$. In particular, the principle decay of $^{137}Cs$ to $^{137}Ba$ results in the emission of monoenergetic gamma-rays of 662 keV. A typically logging-while-drilling (LWD) gamma-ray density tool may include such a radioisotopic source in a drill collar of a borehole assembly. Gamma-ray detectors may be mounted in a tool chassis within the drill collar, which may be surrounded by gamma-ray shielding with openings pointing to windows permissive to gamma-rays in the collar and the stabilizer. The gamma-ray spectral count rate obtained by the gamma-ray detectors may be used to obtain density and photoelectric factor (PEF) corrected for standoff.

The use of radioisotopic sources such as $^{137}Cs$ may be undesirable in logging-while-drilling (LWD) tools. Radioisotopic sources may require special handling when such sources are inserted into or removed from the tool, shielding may be required for transportation and storage of the radioisotopic sources, and security measures may be needed when transporting and storing the radioisotopic sources. Moreover, additional complications may be associated with the abandonment of radioisotopic sources in a well if the LWD tool becomes stuck and cannot be retrieved.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

Embodiments of the present disclosure relate to logging-while-drilling tools and methods involving an electronic radiation generator, such as an electronic X-ray generator. One example of such a logging-while-drilling tool may include a circumferential drill collar, a chassis disposed radially interior to the drill collar, and an electronic X-ray generator and an X-ray detector disposed within the chassis. The electronic X-ray generator may emit X-rays out of the logging-while-drilling tool into a subterranean formation. The X-ray detector may detect X-rays that return to the logging-while-drilling tool after scattering in the subterranean formation, which may be used to determine a density and/or a lithology of the subterranean formation.

Various refinements of the features noted above may exist in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended only to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings in which.

DETAILED DESCRIPTION

Figure 1:
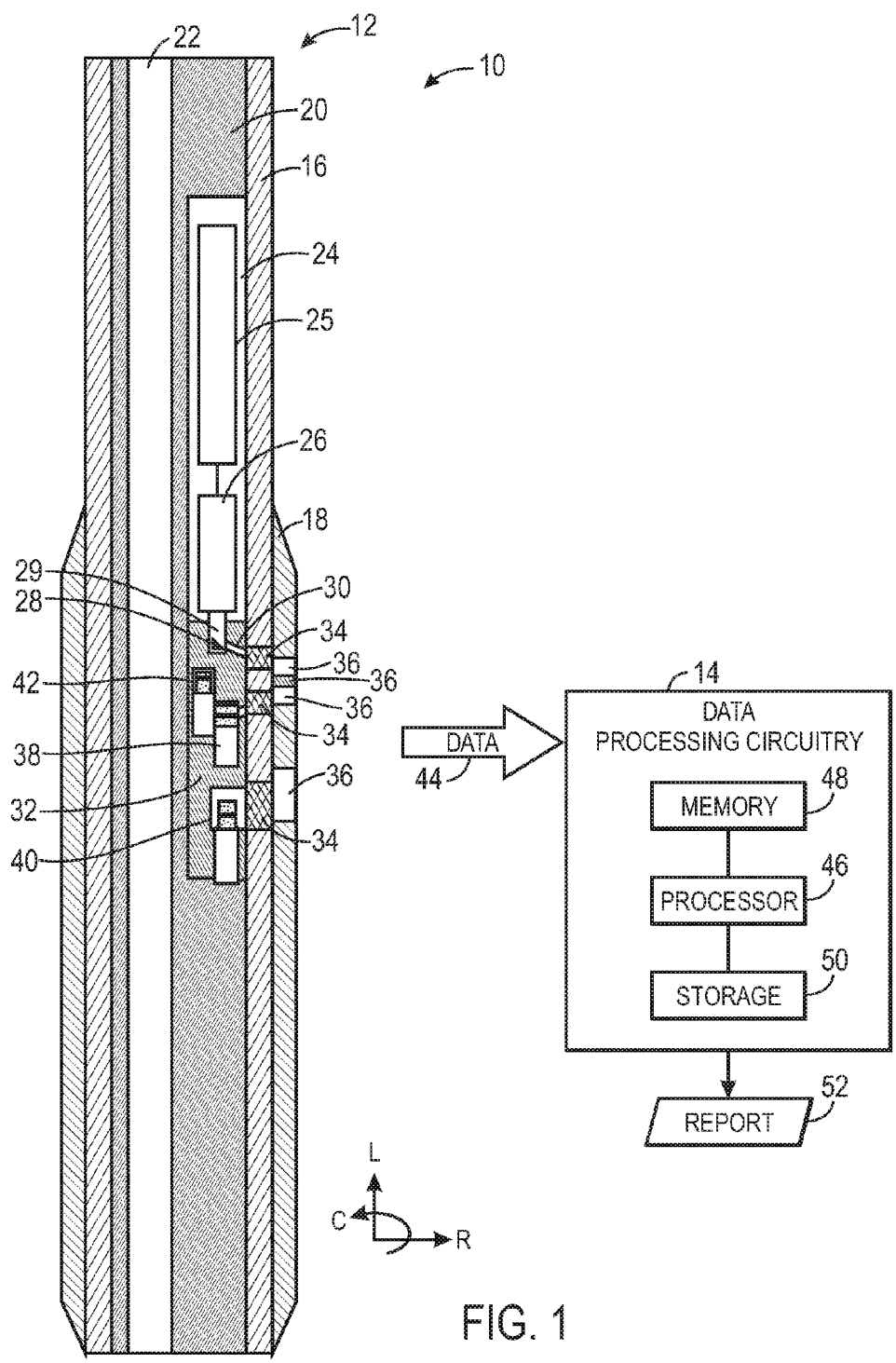
FIG. 1 is a schematic diagram of a logging-while-drilling (LWD) system for obtaining LWD measurements using an X-ray generator integrated into an LWD tool, in accordance with an embodiment.

One or more specific embodiments of the present disclosure will be described below. These described embodiments are only examples of the presently disclosed techniques. Additionally, in an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

Present embodiments relate to a logging-while-drilling (LWD) system that employs an electronic radiation generator, such as an X-ray generator, which may emit X-rays for determining a property of a subterranean formation while drilling. Although the present disclosure provides various examples that discuss an electronic X-ray generator, any other suitable electronic radiation generator emitting radiation with similar characteristics may be employed. The use of an X-ray generator in the LWD tool may improve the performance of formation bulk density and photoelectric factor (PEF) measurements, while avoiding the complications introduced by a radioisotopic source. Moreover, although the energy of the X-rays emitted by the X-ray generator will typically be lower than 662 keV, the X-rays may be suited for better collimation and tighter X-ray detector spacings. With proper collimation of the radiation output by the X-ray generator, in combination with enhanced collimation of the X-ray detector windows, the same or greater depth of investigation (DOI) can be achieved with the LWD tools disclosed herein as with conventional, $^{137}$Cs-based gamma-gamma density LWD tools.

Moreover, a logging-while-drilling (LWD) tool that uses an X-ray generator rather than a radioisotopic source may be capable of performing additional ancillary measurements, such as a measurement of mud density within the mud channel of the LWD tool. In some embodiments, the LWD tool may emit and detect X-rays in more than one azimuthal direction, allowing for a measurement of an azimuthal distribution of properties of the formation. The LWD tool may include, for example, a mandrel-mounted or chassis-mounted X-ray generator and collar-mounted, chassis-mounted, or mandrel-mounted X-ray detectors. Moreover, the LWD tool may additionally or alternatively employ a bipolar X-ray generator or an X-ray generator having a grounded electron source.

With the foregoing in mind, FIG. 1 illustrates a logging-while-drilling (LWD) system 10 that includes an LWD tool 12 and data processing circuitry 14. As will be discussed below, the LWD system 10 may determine a property of a subterranean formation, such as density or lithology, based on Compton scattering and/or the absorption due to photoelectric effect of X-rays emitted into the formation by the LWD tool 12. The data processing circuitry 14, which may determine such properties, may be located within the LWD tool 12, at the surface, or partially within the LWD tool 12 and partially at the surface. Elements of the LWD tool 12 are shown relative to one another according to a coordinate system that includes a longitudinal axis L, a radial axis R, and a circumferential axis C. The longitudinal axis L represents distance along an axis of the LWD tool 12. The radial axis R represents radial distance from the axis of the LWD tool 12 about which the LWD tool 12 rotates during drilling. The circumferential axis C represents a circumferential distance around a radius of the LWD tool 12. This coordinate system appears on other drawings used herein, and should be understood to provide like reference to FIG. 1. In addition, like-numbered elements present in both FIG. 1 and other drawings should be understood to represent like components. As such, many discussions of these like-numbered elements are not reproduced below when these elements appear in other drawings.

The LWD tool 12 may be fitted within a circumferential drill collar 16 of a borehole assembly (BHA), which may include an integrated or attached stabilizer 18 to stabilize the LWD tool 12 when used downhole. Within the drill collar 16, a chassis 20 may hold a mud channel 22 as well as various components for emitting and detecting X-rays. In particular, the LWD tool 12 may include any suitable electronic radiation generator, such as an electronic X-ray generator 24 having a maximum energy of greater than 250 keV. For example, the X-ray generator 24 may be a high voltage X-ray generator such as that disclosed in U.S. Pat. No. 7,564,948, "HIGH VOLTAGE X-RAY GENERATOR AND RELATED OIL WELL FORMATION ANALYSIS APPARATUS AND METHOD," which is assigned to Schlumberger Technology Corporation and incorporated by reference herein in its entirety. Because of an electric potential due to a high voltage generator 25, the X-ray generator 24 may accelerate electrons through an X-ray tube 26 encased in an insulating liquid, gas, or solid. The X-ray tube 26 may be a simple diode with electron source and target 28 or it may be a segmented accelerator structure such as commonly found in Van de Graaf generators. By way of example, such an insulating gas may be $SF_6$. The accelerated electrons may strike the target 28, which may be gold (Au) in certain embodiments, to produce X-rays through Bremsstrahlung radiation. The high voltage generator 25 may be a separate voltage multiplier or it may be built around the X-ray tube 26 such as is common in devices such as dynamitrons. The high voltage generator 25 may be DC or it may be pulsed and, in the pulsed case, the high voltage generator 25 may be a high voltage pulse transformer.

Bremsstrahlung radiation occurs when an electron decelerates in a strong electric field. When an energetic electron accelerated by the X-ray generator 24 enters the target 28, the electron may encounter strong electric fields due to the other electrons present in the target 28. The energetic electron then may decelerate until it has lost all of its kinetic energy, causing the emission of an X-ray. A continuous X-ray energy spectrum may be produced when summed over many decelerated electrons. The maximum X-ray energy will be equal to the total kinetic energy of the energetic electron, and the minimum X-ray energy in the observed Bremsstrahlung spectrum will be that of X-rays just able to exit the target 28 of the X-ray generator. In some embodiments, the X-ray target 28 may emit an X-ray spectrum that peaks at approximately 75% of the maximum beam energy (e.g., approximately 300 keV when the maximum beam energy is 400 keV or approximately 225 keV when the maximum beam energy is 300 keV).

The high voltage generator 25 of the X-ray generator 24 may provide a negative high voltage to the cathode of the X-ray tube 26, while the anodic target 28 of the X-ray tube 26 may be at ground potential. As illustrated in FIG. 1, the target 28 may be recessed within an elongated medal tube 29, which may attach to a ceramic housing of the X-ray tube 26. The elongated medal tube 29 is surrounded by X-ray shielding 32, which may be formed from, for example, high-density tungsten (W).

The shielding 32 may serve several purposes. Among other things, the shielding 32 protects the high voltage insulation of the X-ray generator 24 from being irradiated by large doses of X-rays. Moreover, a source collimator channel 30 formed in the shielding 32 may provide a highly directional beam of X-rays from the target 28 to the materials that surround the LWD tool 12 while suppressing radiation in other directions.

As will be discussed below, some X-rays from the X-ray generator 24 may exit the target 28 and pass into materials that surround the LWD tool 12, such as a surrounding subterranean formation. The X-rays may pass through a collar window 34 and a stabilizer window 36 out of the LWD tool 12. X-rays that return to the LWD tool 12 may pass through other stabilizer windows 36 and collar windows 34 to be detected by X-ray detectors in the LWD tool 12. In the embodiment shown in FIG. 1, the LWD tool 12 includes a near X-ray detector 38 and a far X-ray detector 40 disposed at respective near and far spacings from the target 28, such as approximately 4 inches from the target 28 for the near X-ray detector 38 and approximately 8 inches from the target for the far X-ray detector 40. In other embodiments, any suitable number of X-ray detectors at any suitable spacings may be employed by the downhole tool 12.

The collar windows 34 and the stabilizer windows 36 may only minimally attenuate the X-rays that exit from and return to the LWD tool 12, permitting low energy gamma-rays of approximately 100 keV to be detected in some embodiments. These collar windows 34 and stabilizer windows 36 may take several forms. For example, if the stabilizer 18 is separate from the drill collar 16 (e.g., slip on), the stabilizer windows 36 can be made from a low-density, low-Z material that can survive in the wellbore environment. Since the stabilizer windows 36 are mounted in the stabilizer 18, they will not see any pressure differential. Thus, materials such as polyetheretherketone (PEEK) and polyetherketoneketone (PEKK), as well as many epoxies, may be suitable. The outer surface of the stabilizer windows 36 may be protected to prevent erosion by borehole fluid.

The collar windows 34, which surround the chassis 20, may be designed to support the full pressure of a borehole, which can reach 40,000 PSI. Thus, the collar windows 34 may be metallic materials, such as titanium or titanium alloys, which may offer a low atomic number and low electron density compared to elements found in stainless steel. Alternatively, the collar windows 34 may be constructed of beryllium (Be). However, because Be is not corrosion resistant, Be drill collar windows 34 may be protected by a layer of material that will not corrode. Alternatively, in lieu of the collar windows 34, the drill collar 16 could be thinned down locally on the inside or outside of the LWD tool 12 to facilitate the passage of gamma-rays through the drill collar 16. Advantageously, thinning the drill collar 16 may allow X-rays to pass through the drill collar 16, while maintaining the mechanical integrity of the drill collar 16.

As illustrated in FIG. 1, the shape and size of the collar windows 34 and the stabilizer windows 36 impact the direction and acceptance angles for the outgoing and incoming X-rays. To accentuate this effect, some shielding 32 may surround the collar windows 34 and the stabilizer windows 36 partially or entirely to optimize the collimation (not shown). In addition, shielding 32 may be placed between nearby stabilizer windows 36, as shown in FIG. 1. This further provision of X-ray shielding may prevent X-rays that scatter only in the collar 16 or the stabilizer 18 from reaching the near X-ray detector 38 and causing a background noise signal.

As mentioned above, some X-rays from the X-ray target 28 may exit the LWD tool 12, interact with the surrounding materials, and return to be detected by the near X-ray detector 38 and the far X-ray detector 40. In the example of FIG. 1, the near X-ray detector 38 and the far X-ray detector 40 are scintillation detectors. Since compared to a conventional $^{137}$Cs-based density tool, the average energy of the X-rays emitted from the X-ray generator 24 of the LWD tool 12 are lower, the near X-ray detector 38 and the far X-ray detector 40 may be smaller. In addition, because the X-ray generator 24 may emit a greater quantity of photons than a conventional $^{137}$Cs-based density tool, which may allow the collimator channel 30 to provide a sharper collimation angle while still emitting a useable X-ray flux, the near X-ray detector 38 and far X-ray detector 40 may have shorter spacings. The near X-ray detector 38 and the far X-ray detector 40 may include high-density scintillators such as LuAP:Ce, LuAG:Pr, GSO, or LPS, to name a few, which may be coupled to compact photomultipliers (PMTs). It should be understood that any other suitable X-ray detector could be employed. For example, the near X-ray detector 38 and far X-ray detector 40 may instead use high-temperature semiconductor detectors based on SiC or other suitable materials in lieu of the PMT, or directly as X-ray detectors.

The near X-ray detector 38 and the far X-ray detector 40 may acquire the energy spectrum of the gamma-rays that are detected. This spectral information may be split into a small number (e.g., 2 to 6) of energy windows or "channels," from which density and photoelectric factor (PEF) measurements may be determined. Traditional analog-to-digital converters (ADCs) may be used to split the spectral information into more channels (e.g., 256, 512, etc.) and the channels may be combined to form the desired energy windows. The use of at least two X-ray detectors makes it possible to compensate the density measurement for the effect of standoff from the formation using spine-and-ribs techniques, forward model and inversion techniques, neural networks, or other suitable approaches.

An X-ray monitor 42 may monitor the output and energy of the X-rays emitted by the X-ray generator 24. This measurement by the X-ray monitor 42 can be used to control the quantity and energy of the X-rays output by the X-ray generator 24 using any suitable technique. The X-ray monitor 42, like the X-ray detectors 38 and 40, may include a scintillation detector and an attached photomultiplier (PMT). The X-ray monitor 42 may measure the spectral shape and the total count rate of X-rays that reach the X-ray monitor 42 through the X-ray shield 32. The thickness of the shielding 32 and the distance of the X-ray monitor 42 from the target 28 may be optimized through experimentation or simulation to obtain a good sensitivity to the quantity and energy of the output X-rays of the X-ray generator 24.

Like the X-ray detectors 38 and 40, the X-ray monitor 42 may be any suitable X-ray detector. For example, the X-ray monitor 42 may use high-temperature semiconductor detectors based on SiC or other suitable materials in lieu of the PMT or directly as X-ray detectors. It may be appreciated that the X-ray generator 24 and the X-ray monitor 42 can be considered a single entity, since both are desirable to allow the generation of X-rays with stable endpoint energy and known output quantity.

The responses of the X-ray detectors (e.g., the near X-ray detector 38, the far X-ray detector 40, and the X-ray monitor 42) may be processed by the data processing circuitry 14, and are schematically referred to in FIG. 1 as data 44. The data processing circuitry 14 may include a processor 46, memory 48, and/or storage 50. The processor 46 may be operably coupled to the memory 48 and/or the storage 50 to carry out certain formation-property-determination techniques. These techniques may be carried out by the processor 46 and/or other data processing circuitry based on certain instructions executable by the processor 46. Such instructions may be stored using any suitable article of manufacture, which may include one or more tangible, computer-readable media to at least collectively store these instructions. The article of manufacture may include, for example, the memory 48 and/or the nonvolatile storage 50. The memory 48 and the nonvolatile storage 50 may include any suitable articles of manufacture for storing data and executable instructions, such as random-access memory, read-only memory, rewriteable flash memory, hard drives, and optical disks.

The downhole tool 12 may transmit the data 44 to the data processing circuitry 14 via, for example, internal connections within the tool, a telemetry system communication uplink, and/or a communication cable. After receiving the data 44, the data processing circuitry 14 may determine one or more properties of the subterranean formation that surrounds the downhole tool 12. By way of example, such a formation property may include a photoelectric effect relating to a lithology of the formation or a bulk density of the formation. Thereafter, the data processing circuitry 14 may output a report 36 indicating the one or more ascertained properties of the formation. The report 36 may be stored in memory or may be provided to an operator via one or more output devices, such as an electronic display.

Figure 2:
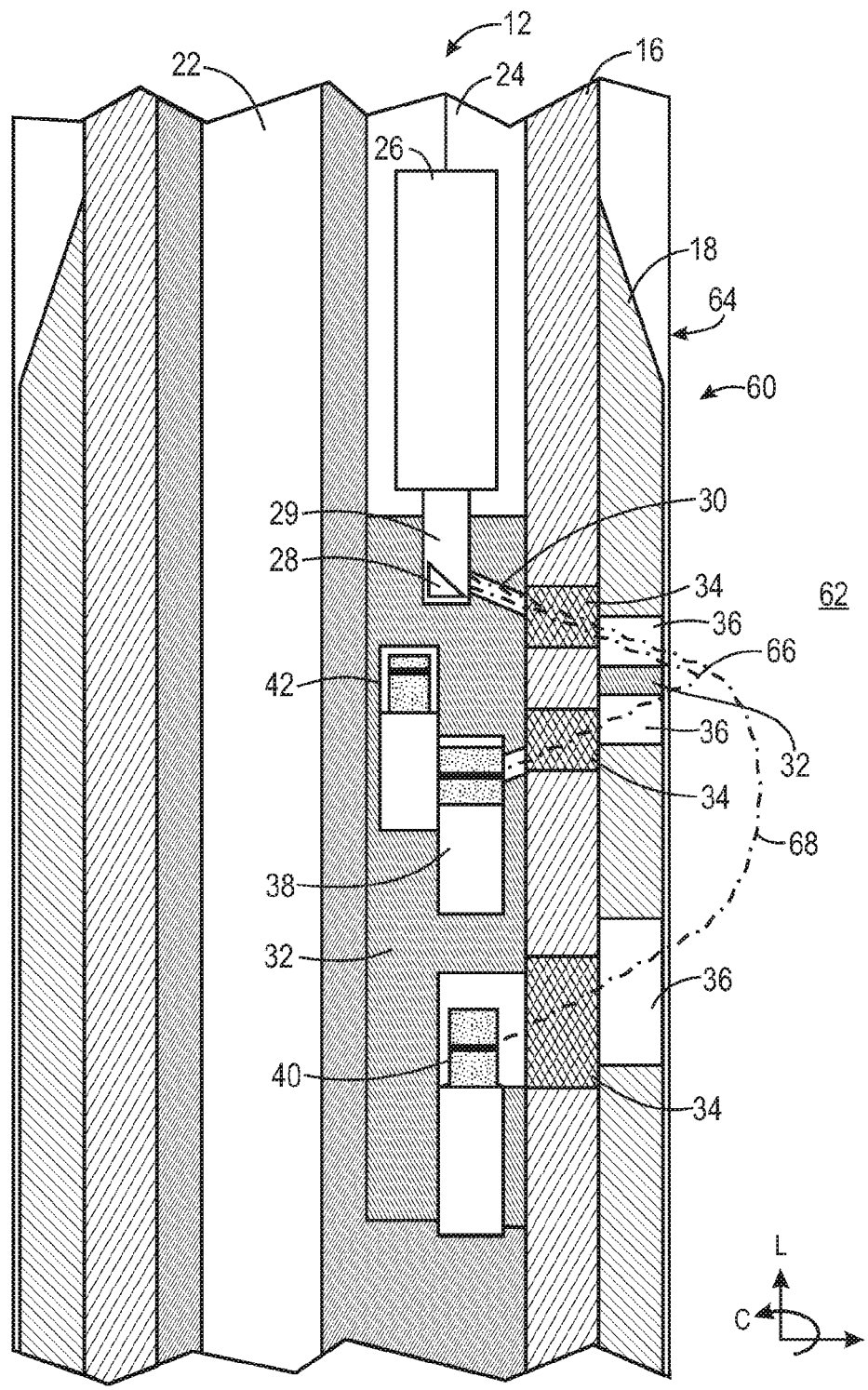
FIG. 2 is a schematic diagram of an LWD operation using the LWD system of FIG. 1, in accordance with an embodiment.

The LWD tool 12 may be used during the process of drilling a well to obtain density and/or photoelectric factor (PEF) measurements of a surrounding subterranean formation. One example of a logging-while-drilling (LWD) operation 60 appears in FIG. 2. In the LWD operation 60, the LWD tool 12 may be used in a borehole assembly (BHA) that is drilling through a subterranean formation 62, creating a borehole 64. Based on the collimation angle of the source collimator 30, the X-rays that are emitted by the source 28 may follow, for example, certain X-rays paths 66 and/or 68. X-rays that generally follow the X-ray path 66 may be detected by the near X-ray detector 38 and may provide information about elements of the formation 62 and/or the borehole 64 at a relatively shallow depth of investigation (DOI). On the other hand, X-rays that generally follow an X-ray path such as the X-ray path 68 may be detected by the far X-ray detector 40 may obtain information about elements of the formation 62 at a relatively deeper DOI.

Figure 3:
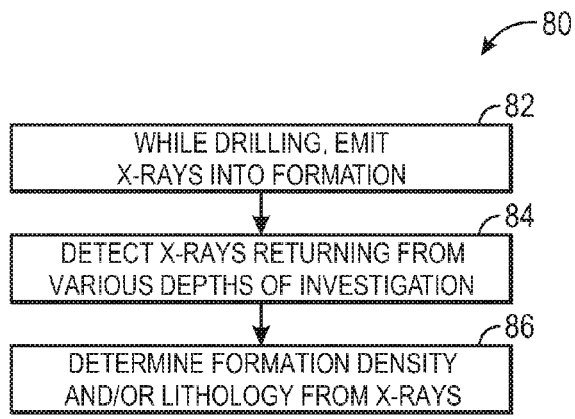
FIG. 3 is a flowchart describing an embodiment of a method for performing the LWD operation of FIG. 2.

One manner in which the LWD operation 60 may be carried out is represented by a flowchart 80 of FIG. 3. The flowchart 80 may begin while a borehole 64 is being drilled into a formation 62 using a borehole assembly (BHA) that includes the LWD tool 12. The X-ray generator 24 of the LWD tool 12 may emit X-rays into the formation 62 (block 82). Subsequently, X-ray detectors in the LWD tool 12, such as the near X-ray detector 38 and the far X-ray detector 40, may detect X-rays that return to the LWD tool 12 from various depths of investigation after Compton scattering with elements of the formation 62 (block 84). Based on the X-rays detected by the X-ray detectors of the LWD tool 12, the data processing circuitry 14 may determine a formation density of the formation 62 and/or a lithology based on photoelectric factor (PEF) using any suitable technique (block 86).

Figure 4:
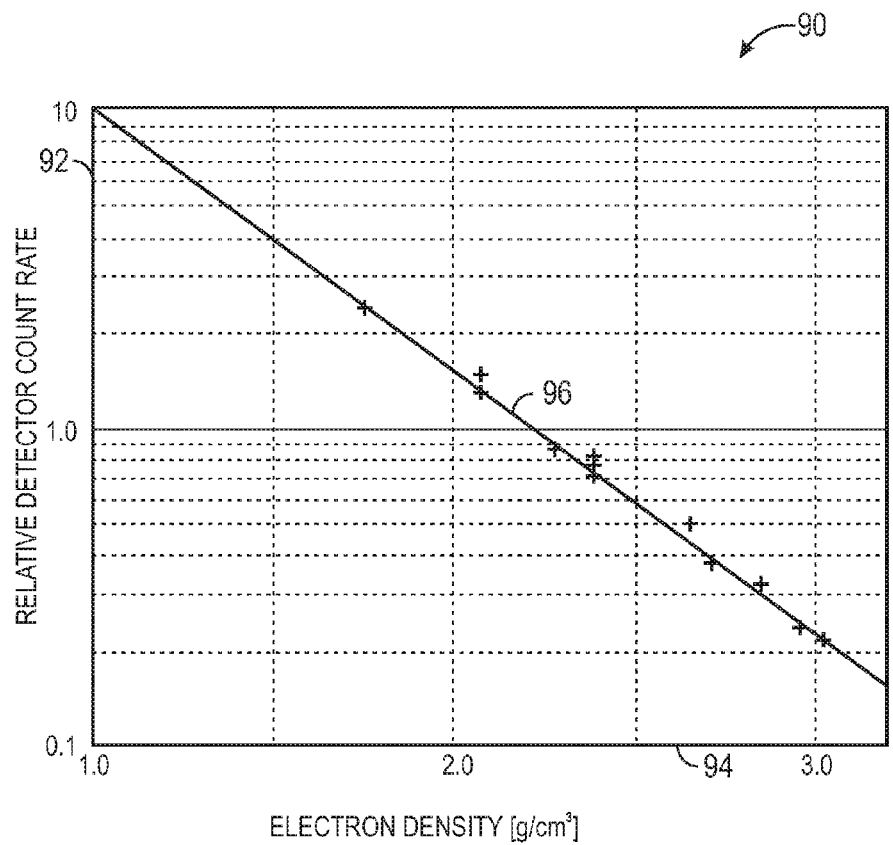
FIG. 4 is a plot of a density spine of a far-spaced detector of the LWD tool of FIG. 1, obtained through modeling, in accordance with an embodiment.

When the LWD tool 12 is used to determine a property of the formation 62, such as the density of the formation 62, the LWD tool 12 may produce similar results to that of a conventional $^{137}$Cs-based density tool. For example, a plot 90 of FIG. 4 illustrates a relationship between relative count rate and formation electron density using the far detector 40 of the LWD tool 12. In the plot 90, an ordinate 92 represents relative count rates obtained from the X-ray detector 40 and an abscissa 94 represents an electron density of the formation 62 in units of g/cm³. A curve 96 has been fit to various data points to represent a density spine of the far X-ray detector 40. It should be appreciated that the curve 96 is very similar to a curve that would be obtained using a conventional $^{137}$Cs-based tool.

Figure 5:
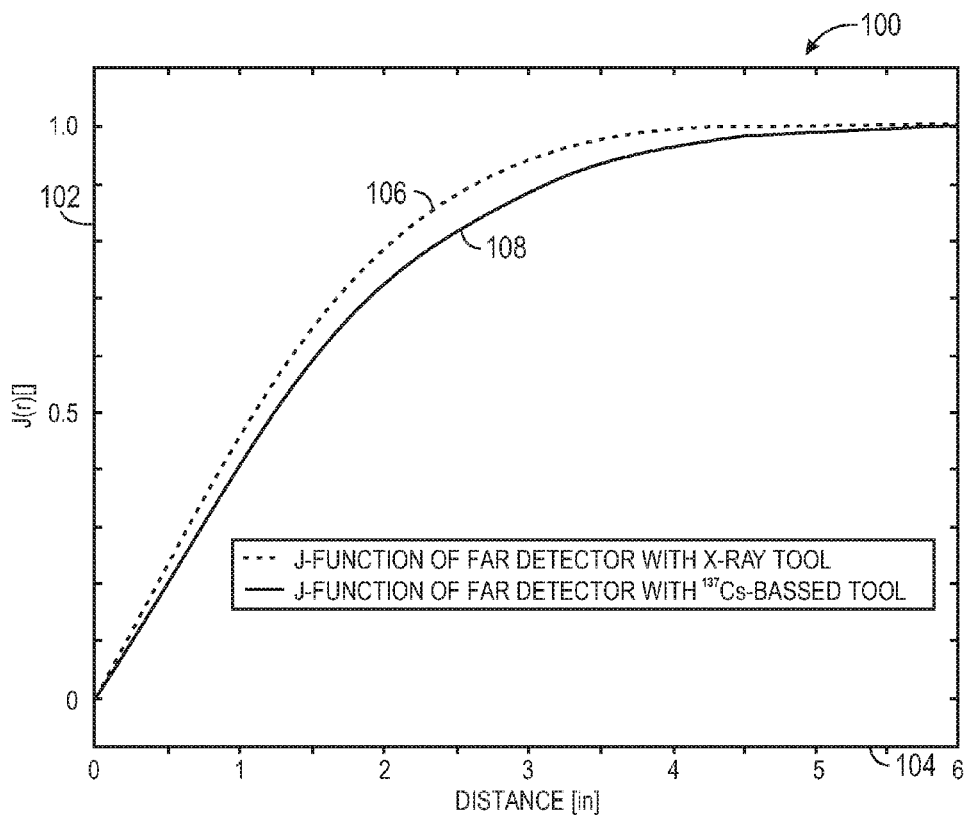
FIG. 5 is a plot of a depth of investigation (DOI) of the far-spaced X-ray detector of the LWD tool of FIG. 1 as to compared to that of a conventional $^{137}Cs$-based tool, obtained through modeling, in accordance with an embodiment.

The depth of investigation (DOI) of such a measurement is modeled in a plot 100 of FIG. 5. An ordinate 102 of the plot 100 represents J-function and an abscissa 104 represents the depth of investigation in units of inches. A curve 106 represents the J-function of the far X-ray detector 40 and a curve 108 represents a J-function of a far detector in a conventional $^{137}$Cs-based tool. As illustrated by FIG. 5, the curves 106 and 108 are very similar. Indeed, it is believed that with optimized collimation, the LWD tool 12 can match the depth of investigation of a conventional $^{137}$Cs-based tool while maintaining equal or better precision.

Figure 6:
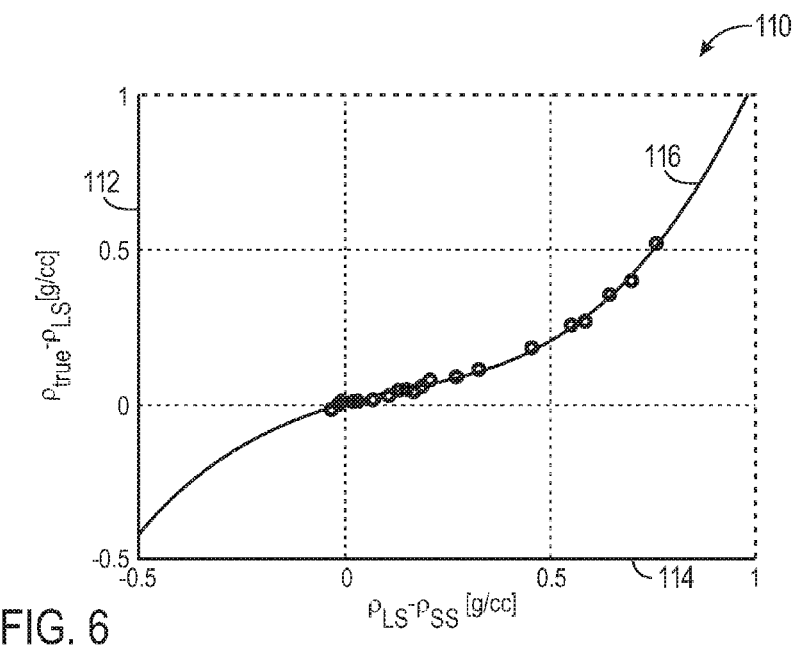
FIG. 6 is a plot of spine and ribs data associated with the LWD tool of FIG. 1, obtained through modeling, in accordance with an embodiment.

FIG. 6 represents an example of a spine-and-ribs plot 100 for the two-X-ray-detector configuration of the LWD tool 12 shown in FIG. 1. An ordinate 112 represents the true formation density $\rho_{true}$ of the formation 62 and an abscissa 114 represents the correction to the apparent density $\rho_{LS}$ ($\rho_{LS}-\rho_{SS}$) obtained by a LS detector (e.g., the far X-ray detector 40 of FIG. 1). As shown by a curve 116 of the plot 110, the LWD tool 12 can match and exceed the performance of a conventional $^{137}$Cs-based tool. Indeed, FIG. 6 shows the correction to the apparent density $\rho_{LS}$ obtained by a LS detector (e.g., the far X-ray detector 40 of FIG. 1) to obtain the true formation density $\rho_{true}$ for different amounts of stand off in muds with different densities and PEF as a function of the difference between the apparent densities $\rho_{LS}$ and $\rho_{SS}$. The obtained function is very similar to the equivalent function obtained with $^{137}$Cs-based tool. One significant advantage is that a much higher photon output can be achieved with the X-ray generator 24 than with a conventional radioisotopic gamma-ray source that could be handled and transported safely. It is estimated that with an X-ray generator 24 running at 300 keV, a precision improvement of at least a factor of two over a traditional $^{137}$Cs-based density tool can be achieved at the same drilling speed (ROP).

A number of variations of the LWD tool 12 shown in FIG. 1 are envisaged. For example, a configuration 130 of the LWD tool 12, which appears in FIG. 7, includes four X-ray detectors 132, 134, 136, and 138. The four X-ray detectors 132, 134, 136, and 138 are encased in shielding 32 in the chassis 20 of the LWD tool 12. It should be noted that, in the configuration 130, the first X-ray detector 132 and the second X-ray detector 134 share a single collar window 34 and stabilizer window 36, but receive X-rays through different collimation channels 140 and 142. These collimation channels 140 and 142 collimate X-rays entering the shared collar window 34 and stabilizer window 36 at different angles. Because the collimation channels 140 and 142 receive X-rays that enter the LWD tool 12 at different angles, the first X-ray detector 132 may detect X-rays from a different depth of investigation than those detected by the second X-ray detector 134. In the configuration 130 shown in FIG. 7, an X-ray monitor 42 is present in the same longitudinal plane as the X-ray target 28. However, the X-ray monitor 42 may be located in a circumferential location not visible in FIG. 7.

Figure 7:
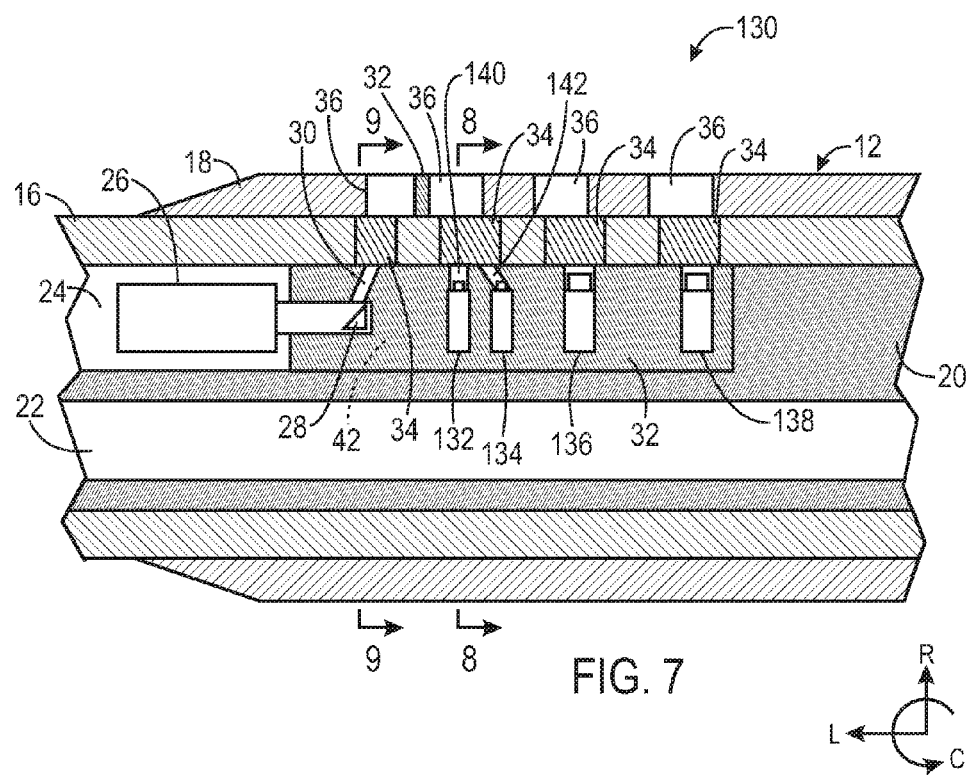
FIG. 7 is a schematic diagram of a configuration of an LWD tool employing an X-ray generator and four X-ray detectors, in accordance with an embodiment.
Figure 8:
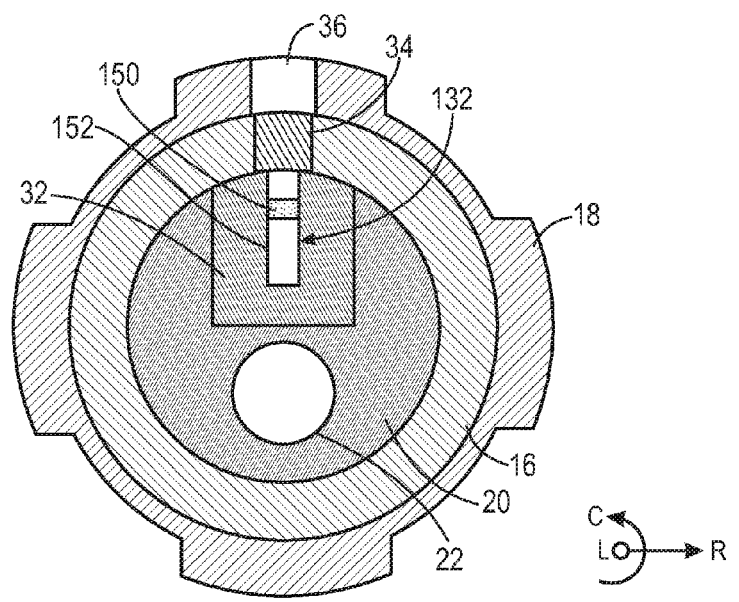
FIGS. 8 and 9 are cross-sectional views of the LWD tool configuration of FIG. 7, in accordance with an embodiment.
Figure 9:
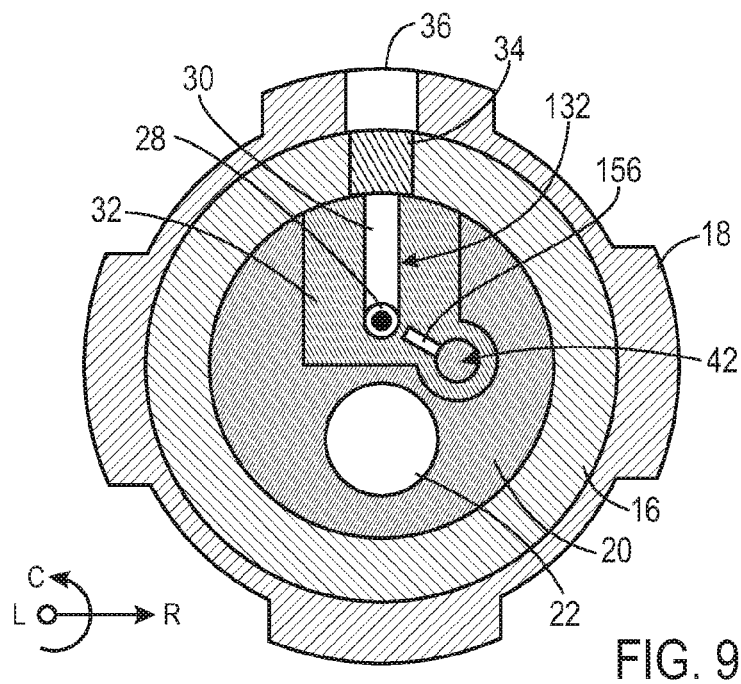

FIGS. 8 and 9 represent cross-sectional views at cut lines 8-8 and 9-9 of FIG. 7, respectively. FIG. 8 represents particularly a cross-section of the configuration 130 of the LWD tool 12 at the location of the first X-ray detector 132. As seen in FIG. 8, the first X-ray detector 132 may include a scintillator 150 and a photomultiplier tube (PMT) 152. The first X-ray detector 132 may be surrounded by X-ray shielding 32, which may not occupy all of the circumferential space in the chassis 20 of the LWD tool 12 at the axial or longitudinal location of the first X-ray detector 132. Rather, as shown in FIG. 8, the shielding 32 may only surround the first X-ray detector 132 and other materials may fill the remainder of the chassis 20.

In FIG. 9, which represents a cross-sectional view of the configuration 130 of the LWD tool 12 at cut lines 9-9 of FIG. 7, the circumferential disposition of the X-ray monitor 42 relative to the X-ray target 28 is apparent. Namely, the X-ray monitor 42 may be disposed alongside in the same overlapping axial or longitudinal location as (i.e., at a different circumferential location from) the X-ray target 28 in the chassis 20 depicted along cut lines 9-9 of FIG. 7. The X-ray monitor 42 may include monitor shielding 32 and a monitor channel 156 through the shielding 32 as depicted.

As can be seen in FIG. 9, additional circumferential space remains in the chassis 20 at the axial or longitudinal location of the target 28. An alternative embodiment, illustrated in FIG. 10, employs this additional circumferential space to hold an X-ray detector 157 that may detect X-rays returning from the mud channel 22. Specifically, a secondary collimation channel 158 may guide some X-rays from the target 28 into the mud channel 22, where the X-rays may Compton scatter and/or be absorbed through the photoelectric effect by elements in the fluid flowing through the mud channel 22. The X-ray detector 157 may be surrounded by shielding 32 on all sides except for a collimation channel 159, which may channel X-rays scattered in the mud channel 22 to the X-ray detector 157. The X-rays that are detected by the X-ray detector 157 may allow the determination of certain properties (e.g., density and/or photoelectric factor (PEF)) of the fluid in the mud channel 22.

Figure 10:
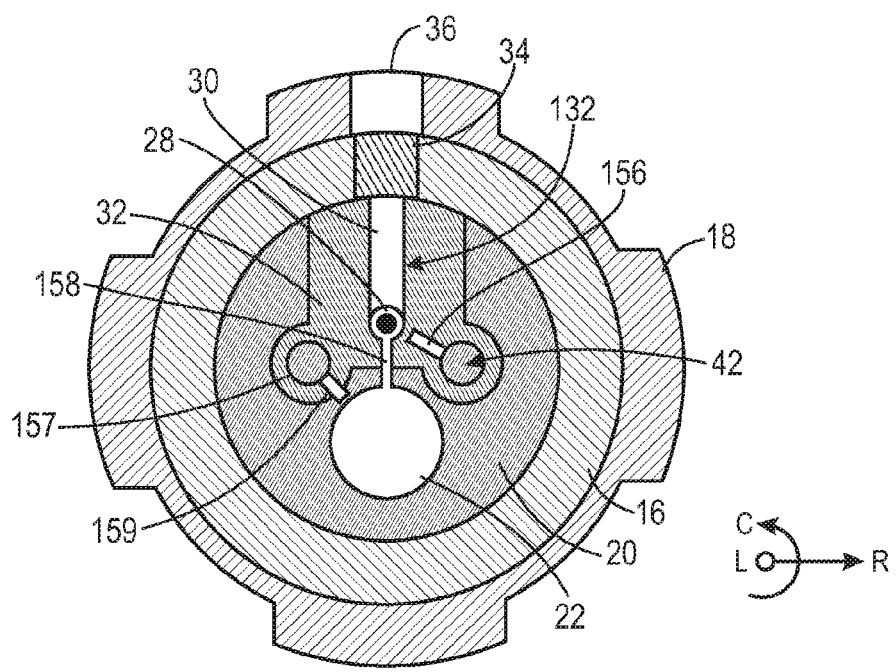
FIG. 10 is a cross-sectional view of an alternative configuration of the LWD tool of FIG. 7, in accordance with an embodiment.

In an alternative approach to FIG. 10, the X-ray detector 157 may be mounted near the mud channel 22 generally opposite, but not necessarily completely opposite, the X-ray target 28 at the same or similar axial position. Such an approach may allow a direct transmission attenuation measurement of the X-rays in the mud channel 22. The radiation incident in the mud channel 22 could be filtered appropriately to enhance the sensitivity. The angle of incidence of the x-rays on the mud channel 22 does not have to be perpendicular to the axis of the LWD tool 12 or of the mud channel 22. Indeed, a smaller angle may be preferable to increase the length of mud traversed by the incident radiation and thus increase the sensitivity. It should further be appreciated that this approach could alternatively take place using a mandrel-mounted configuration, but given the short distance through the mud channel 22 in a mandrel-mounted configuration, the measurement may not be as accurate.

In another embodiment, the X-ray generator 24 may be mounted in a mandrel of the LWD tool 12. For example, as shown by a configuration 160 of FIG. 11, the X-ray generator 24 may be located within a mandrel pressure housing 162 in a mandrel chassis 164. In the configuration 160, the X-ray generator 24 and the X-ray monitor 42 are mounted in the mandrel chassis 164, which is centered in the flow channel and surrounded by the mud channel 22. The centralization of the mandrel chassis 22 is provided by certain mandrel supports 166, which may be short and narrow to avoid restricting the mud flow through the mud channel 22. X-rays generated by the X-ray detector 24 may pass through a source collimation channel 167, a mandrel support 166, a drill collar window 34, and a stabilizer window 36 to exit the LWD tool 12. The mechanical demands on the drill collar window 34 and stabilizer window 36 may be reduced because these windows 34 and 36 only have to support the pressure differential between the mud channel 22 and the borehole outside of the LWD tool 12.

Figure 11:
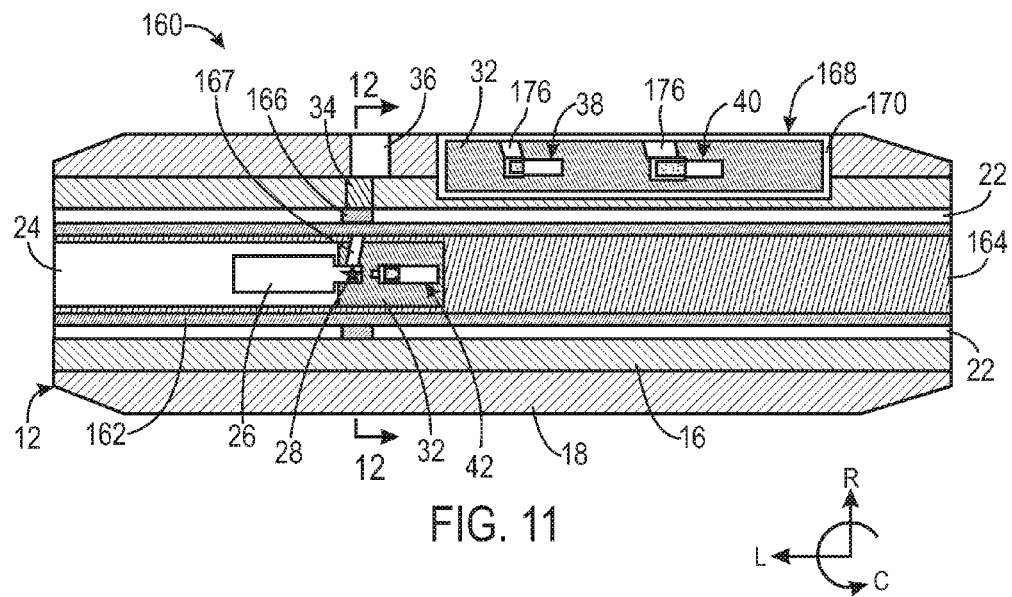
FIG. 11 is a schematic diagram illustrating a configuration of an LWD tool employing a mandrel-mounted X-ray generator and collar-mounted X-ray detectors, in accordance with an embodiment.

The X-rays emitted from out of the configuration 160 of the LWD tool 12 may be detected by a collar-mounted X-ray detector group 168. The collar-mounted X-ray detector group 168 appears in a distinct collar-mounted X-ray detector housing 170 that surrounds a near X-ray detector 38 and a far X-ray detector 40 in X-ray shielding 32. The collar-mounted X-ray detector housing 170 may be formed from titanium, as there may not be enough room in the collar 16 and/or stabilizer 18 to include separate X-ray windows. Although only a near X-ray detector 38 and a far X-ray detector 40 are shown in the example of FIG. 11, additional X-ray detectors may be included in alternative embodiments. It may be appreciated that mounting the X-ray detectors 38 and 40 in the collar 16 and stabilizer 18 may improve their measurement precision.

Figure 12:
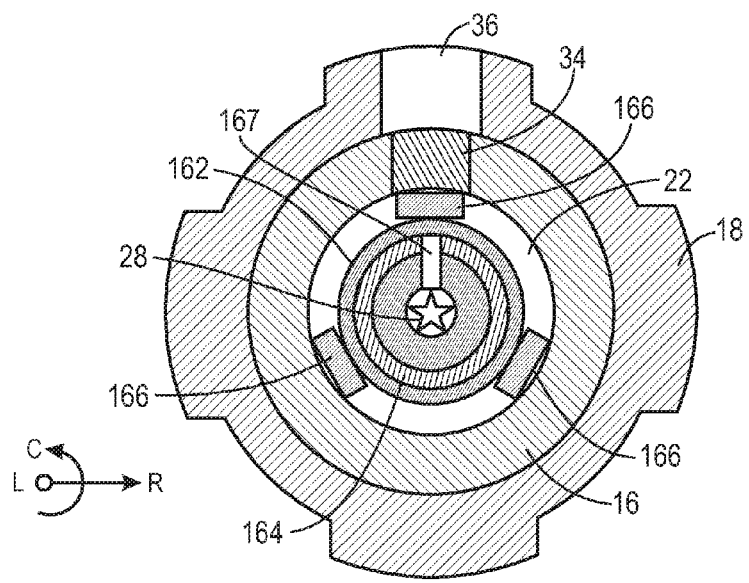
FIG. 12 is a cross-sectional schematic diagram of the LWD tool configuration of FIG. 11, in accordance with an embodiment.

A cross-sectional view of the configuration 160 along cut lines 12-12 of FIG. 11 appears in FIG. 12. As shown in FIG. 12, the target 28 may be located in the center of the mandrel chassis 164, which is surrounded by the mandrel housing 162. Mandrel supports 166 may be spaced at circumferential locations around the mandrel housing 162 in a manner that minimally disrupts mud flow through the mud channel 22. X-rays generated by the X-ray target 28 may exit through the collimation channel 167 and pass through a mandrel support 166, a collar window 34, and a stabilizer window 36.

Figure 13:
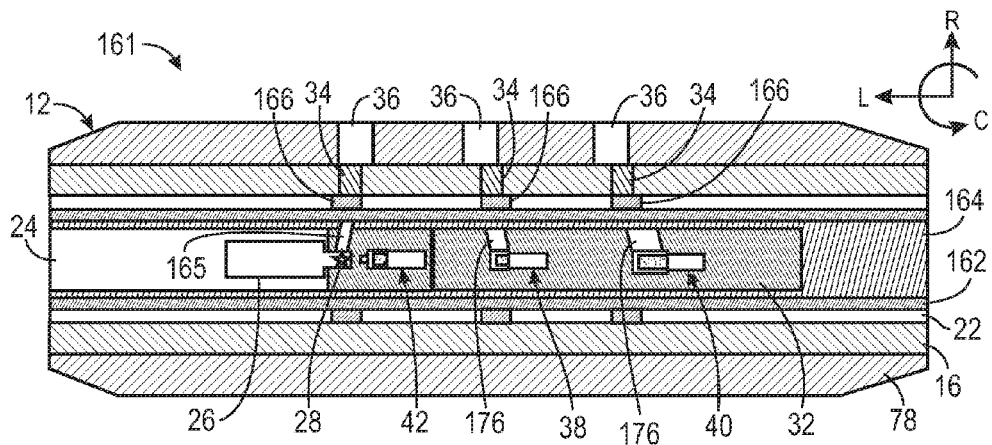
FIG. 13 is a schematic diagram illustrating a configuration of an LWD tool employing a mandrel-mounted X-ray generator and mandrel-mounted X-ray detectors, in accordance with an embodiment.

In some embodiments, such as the configuration 161 of the LWD tool 12 of FIG. 13, X-ray detectors (e.g., the near X-ray detector 38 and the far X-ray detector 40) may be located within the mandrel chassis 164 with the X-ray generator 24. In certain embodiments, the mandrel pressure housing 162 may be made of titanium to facilitate the transmission of low-energy X-rays out of the LWD tool 12 from the target 28 and into the LWD tool 12 from outside the LWD tool 12. Alternatively, windows in the mandrel housing 162 (not shown) of an X-ray transmissive material could be placed in line with the mandrel supports 166, drill collar windows 34, and stabilizer windows 36.

Figure 14:
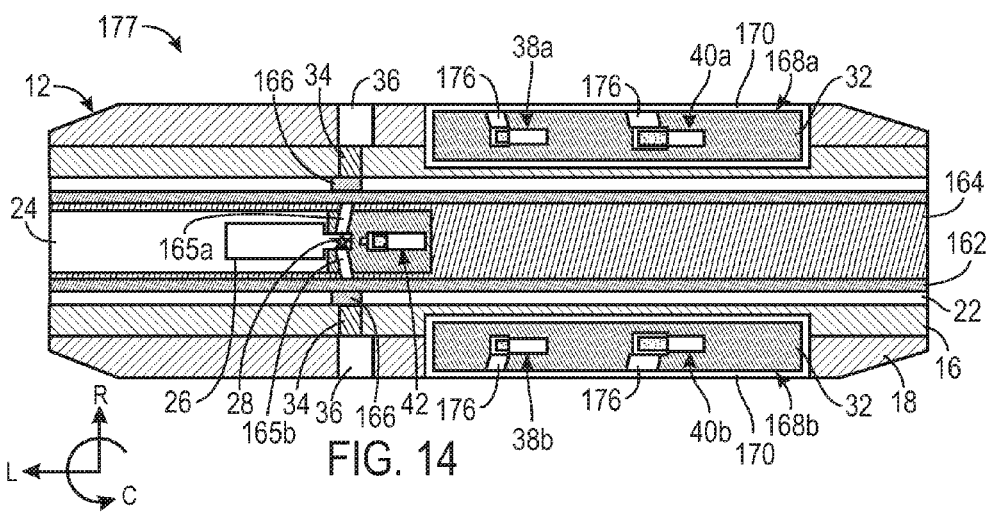
FIG. 14 is a schematic diagram of a configuration of an LWD tool employing a mandrel-mounted X-ray generator that emits X-rays in more than one azimuthal direction out of the LWD tool, in accordance with an embodiment.

When collar-mounted X-ray detector groups 168 are employed, some embodiments may include more than one set of collar-mounted X-ray detector groups 168. For example, a configuration 177 of the LWD tool 12 is shown in FIG. 14 that includes two collar-mounted X-ray detector groups 168A and 168B disposed at different circumferential locations of the LWD tool 12. The X-ray generator 24 may be mounted within the mandrel chassis 164, and two collimation channels 165A and 165B in the shielding 32 in the mandrel chassis 164 may guide collimated X-rays out of the LWD tool 12 at two distinct azimuthal angles from the LWD tool 12. In the configuration 177, because the circumferential locations of the collar-mounted X-ray detector groups 168A and 168B are opposite each other, the two azimuthal angles are approximately 180 degrees apart. However, in alternative embodiments, any suitable circumferential locations for the collar-mounted X-ray detector groups 168A and 168B may be selected, such that X-rays from any suitable azimuthal angle may be detected.

Each of the collar-mounted X-ray detector groups 168A and 168B may include respective near X-ray detectors 38A and 38B and far X-ray detectors 40A and 40B. It should be understood that any suitable number of collar-mounted X-ray detector groups 168 may be employed in alternative configurations, which may be placed at any suitable circumferential locations in the collar 16. For example, in some alternative embodiments three collar-mounted X-ray detector groups 168 may be azimuthally disposed 120 degrees apart from one another and, in certain of these embodiments, three collimation channels 165 may output collimated X-rays at three respective azimuthal angles. It should be appreciated that when more than one collar-mounted X-ray detector group 168 is used in the LWD tool 12, such as the example shown in FIG. 14, simultaneous measurements at multiple azimuths may be possible. Thus, to provide one example, azimuthal density can be measured when the LWD tool 12 is sliding.

Figure 15:
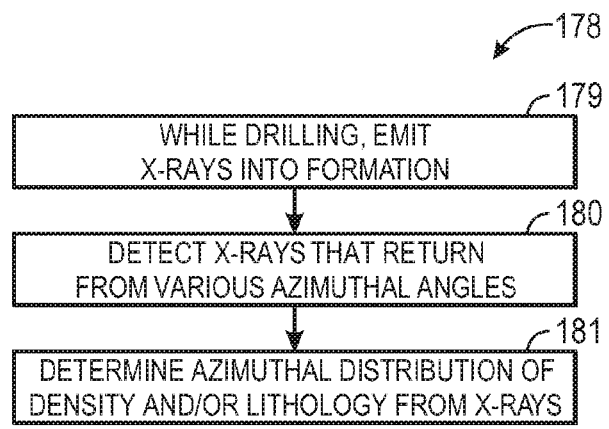
FIG. 15 is a flowchart describing an embodiment of a method for performing an LWD operation using a configuration of the LWD tool such as that shown in FIG. 14.

As noted above, a configuration of the LWD tool 12 that detects X-rays from multiple azimuthal angles, such as the configuration 177 of FIG. 14, may enable the determination of an azimuthal distribution of some properties of the subterranean formation 62. For example, a flowchart 178 of FIG. 15 represents an LWD operation that begins when a borehole 64 is being drilled into a formation 62 using a borehole assembly (BHA) that includes the LWD tool 12. The X-ray generator 24 of the LWD tool 12 may emit X-rays into the formation 62 in multiple azimuthal directions (block 179). Subsequently, X-ray detectors at various circumferential locations in the LWD tool 12, such as the collar-mounted X-ray detector groups 168A and 168B of the configuration 177, may detect X-rays that return to the LWD tool 12 from different azimuthal angles after Compton scattering with elements of the formation 62 (block 180). Based on the X-rays detected by the X-ray detectors of the LWD tool 12, the data processing circuitry 14 may determine a distribution of formation 62 properties (e.g., formation density of the formation 62 and/or a lithology based on photoelectric factor (PEF)) using any suitable technique (block 181).

Many other embodiments are envisioned. When the LWD tool 12 has a sufficiently large collar 16, it may be possible to embed both the X-ray generator 24 and the X-ray detectors (e.g., the near X-ray detector 38 and the far X-ray detector 40). By way of example shown in FIGS. 22 and 23, a configuration 290 of the LWD tool 12 includes a pressure housing 291 that may be embedded in the collar 16 of the LWD tool 12. Such a pressure housing 291 may include not only the X-ray detectors 38 and 40 but also the X-ray generator 24 and X-ray monitor 42.

Figure 22:
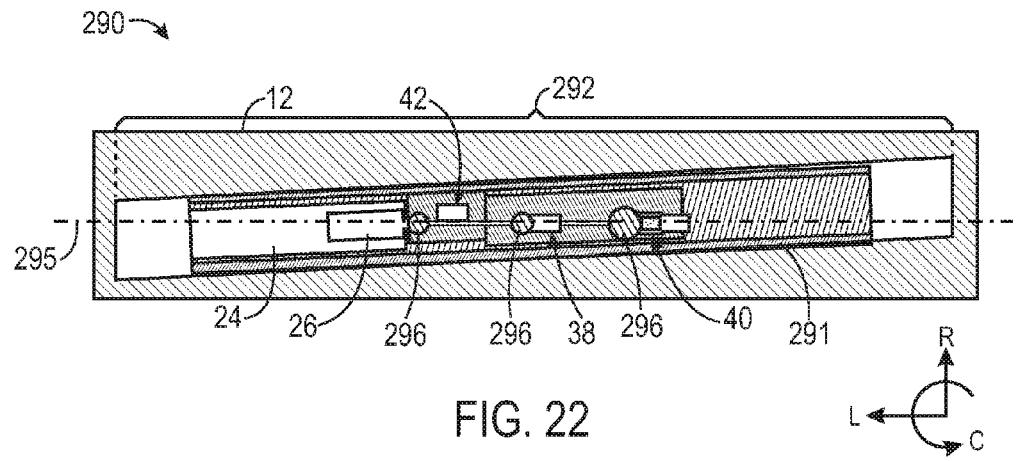
FIGS. 22 and 23 are schematic diagrams of top and side views of a configuration of an LWD tool having an X-ray generator and X-ray detectors mounted in an integrated stabilizer, in accordance with an embodiment.
Figure 23:
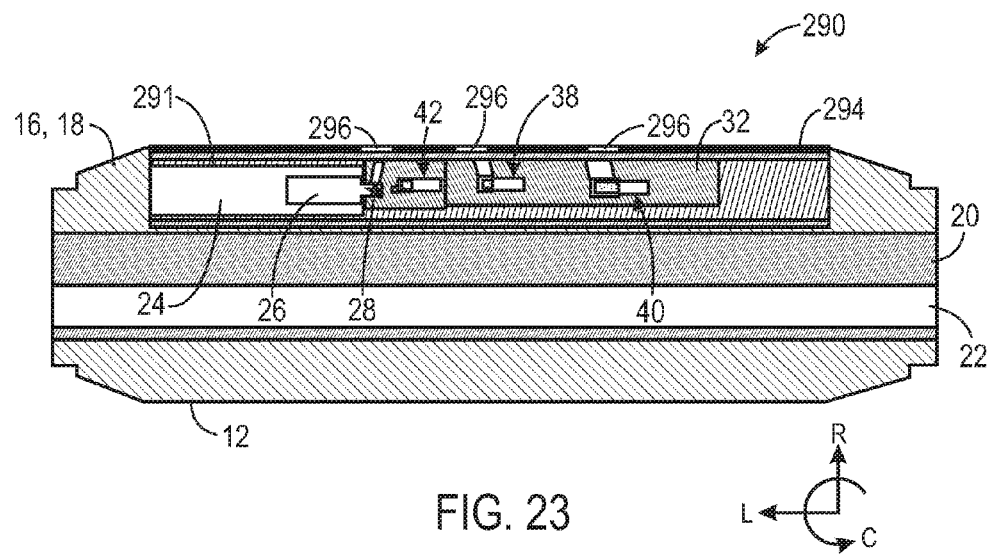

FIGS. 22 and 23 respectively illustrate top and side views of the pressure housing 291 mounted in an integrated stabilizer 292 of the LWD tool 12. The X-ray generator 24, including the X-ray tube 26, and X-ray detectors 38 and 40 may be contained in a pressure housing 291 that is embedded in a blade of the integrated stabilizer 292 and covered by a wear-protective cover 294, which may be a metal plate. The blade of the stabilizer 292 may form a non-zero angle with the LWD tool 12 axis 295. However, it is preferable that source and detector windows 296 be aligned along the axis 295, as shown in FIG. 22. Additionally or alternatively to being covered by the wear-protective cover 294, a protective layer could be added directly to the pressure housing 291. If such a protective layer is made of tungsten carbide, it should not cover the region of the detector windows 296. An alternative wear protection using a low-Z material like Chrome Carbide could be used. Instead of using windows 296, the pressure housing 291 could be made of high strength titanium to allow sufficient transparency for low-energy X-rays.

Figure 24:
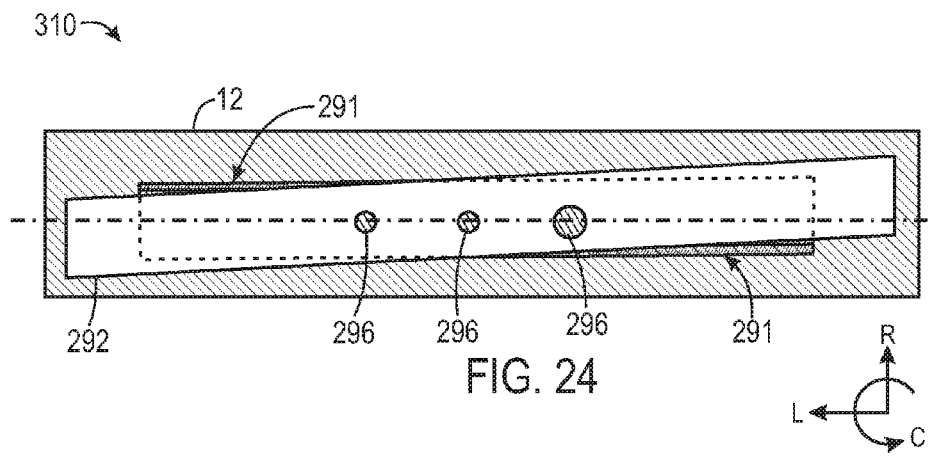
FIGS. 24 and 25 are schematic diagrams of top and side views of a configuration of an LWD tool having an X-ray generator and X-ray detectors mounted in a hole drilled off-center in a drill collar of the LWD tool, in accordance with an embodiment.
Figure 25:
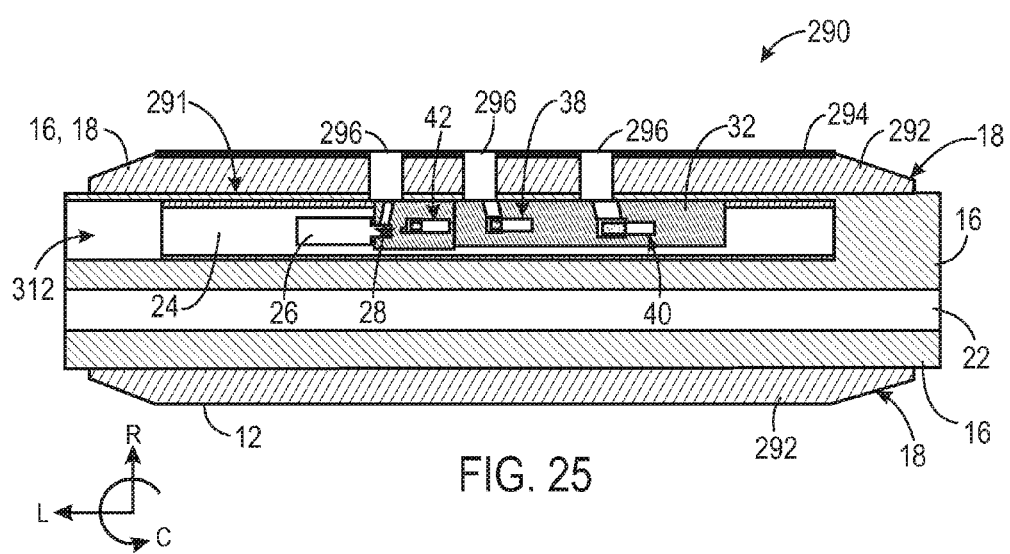

Alternatively, as shown by a configuration 310 of FIGS. 24 and 25, in an LWD tool 12 having a collar with a sufficiently small interior diameter (ID) relative to the drill collar 16, X-ray detectors (e.g., a near X-ray detector 38 and far X-ray detector 40) and the X-ray generator 24 could be housed in a hole 312 drilled off-center in the collar 16. For such an embodiment, windows 296 may be used to reduce the absorption of low-energy X-rays.

Figure 26:
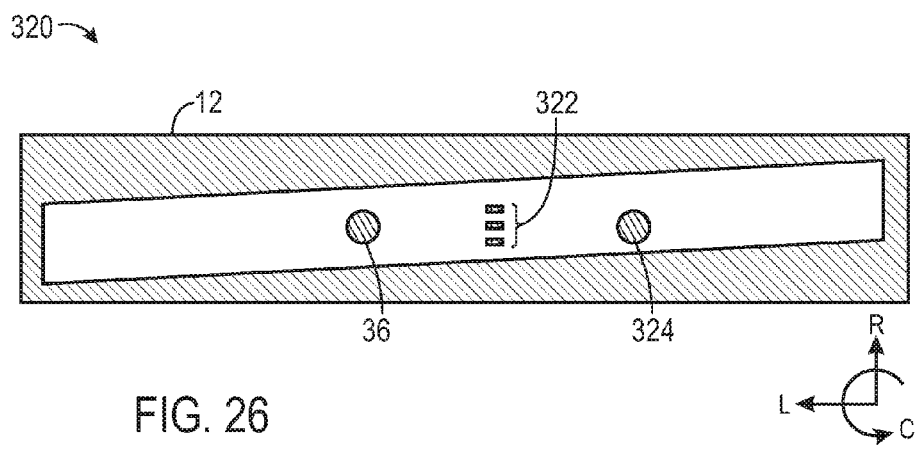
FIGS. 26-28 are schematic diagrams of top, side, and cross-sectional views of a configuration of an LWD tool having multiple azimuthally adjacent X-ray detectors, in accordance with an embodiment.
Figure 27:
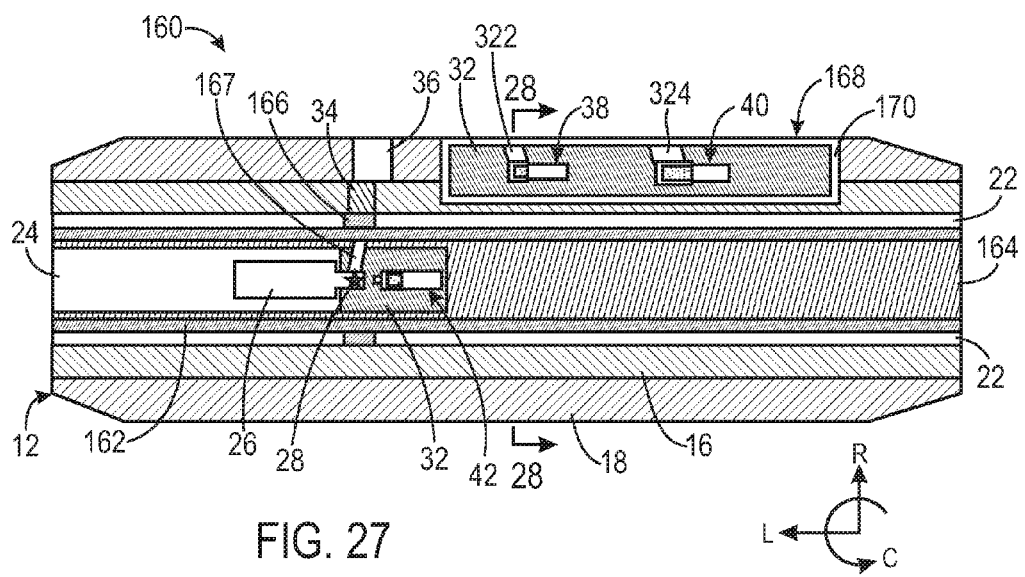
Figure 28:
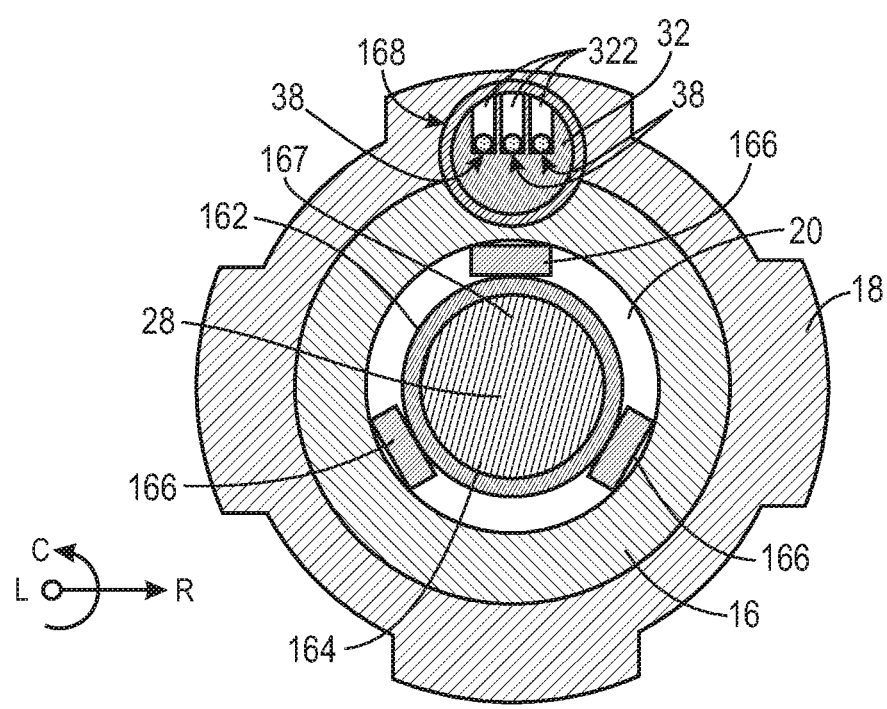

In yet another embodiment represented by a configuration 320 of the LWD tool 12 of FIGS. 26-28, the same pressure housing 168 in the collar 16 could contain several azimuthally adjacent X-ray detectors 38. As seen in FIGS. 26-28, only the X-ray detectors 38 and 40 may be mounted in the collar 16 (see also FIG. 11). Instead of a single near X-ray detector 38, three adjacent near X-ray detectors 38 with separate (narrow) collimation channels 322 are employed to enhance the azimuthal resolution. Alternatively, a position-sensitive X-ray detector could be used. The cross-sectional view at the near detector, at cut lines 28-28 of FIG. 27, is shown in FIG. 28. In FIG. 28, the three azimuthally adjacent near X-ray detectors 38 and the three azimuthally adjacent collimation channels can be seen. It should be understood that alternative embodiments may include more or fewer azimuthally adjacent X-ray detectors 38 and/or may include azimuthally adjacent far X-ray detectors 40 or other azimuthally adjacent X-ray detectors. It may be appreciated that the configuration 320 of FIGS. 26-28 could lead to better image results as single collimator openings for the X-ray detectors 38 and/or 40 could be reduced and replaced by multiple narrow collimator channels 322 or 324 at the same location. Multiple adjacent X-ray detectors could be limited to one distance (e.g., near) from the X-ray target 28. Thereafter, a technique such as alpha processing could be used to extract a high-resolution image.

Figure 16:
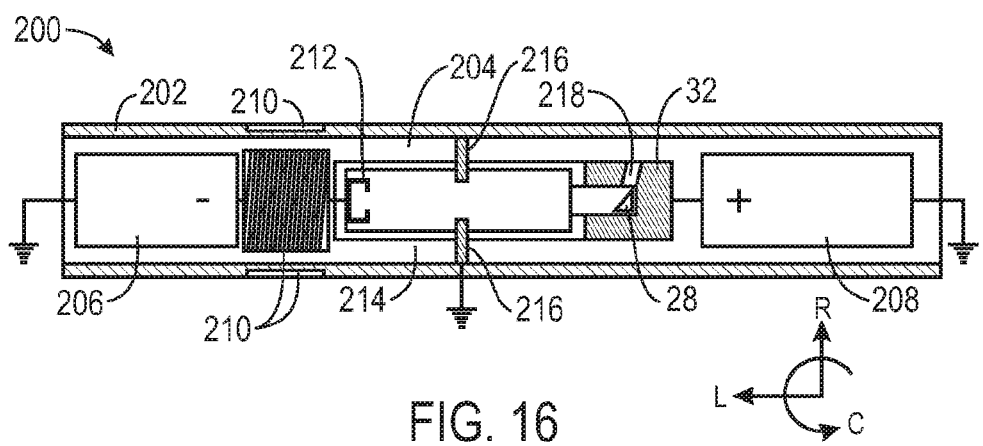
FIG. 16 is a schematic diagram of a bipolar X-ray generator, in accordance with an embodiment.

Some configurations of the LWD tool 12 may employ an X-ray generator having a dual-polarity power supply. One example of such an X-ray generator having a dual-polarity power supply appears in FIG. 16, which illustrates a bipolar X-ray generator 200. Such a bipolar X-ray generator 200 may be incorporated in an annular configuration such as shown in FIGS. 1, 2, and 7-10, or a mandrel-mounted configuration, such as those shown in FIGS. 11-14. The bipolar X-ray generator 200 may include a housing 202 of a material relatively transmissive to X-rays, which may include high voltage insulation 204 and a variety of components. Among other things, the housing 202 may encase a negative high voltage power supply 206 and a positive high voltage power supply 208. The negative high voltage power supply 206 may be coupled to a cathode power supply transformer 210 that adjoins an electron source 212 in an X-ray tube 214. The positive high voltage power supply 208 may be coupled to the target 28. A grounded electrode 216 may be located within the X-ray tube 214 to cause an electric potential to vary relatively smoothly between the electron source 212 at low potential and the target 28 at high potential. As mentioned above, electrons from the electron source 212 may accelerate through the X-ray tube 214, striking the target 28 and producing X-rays through Bremsstrahlung radiation. The X-rays may be emitted through a collimation channel 218 in the bipolar X-ray generator 200.

Figure 17:
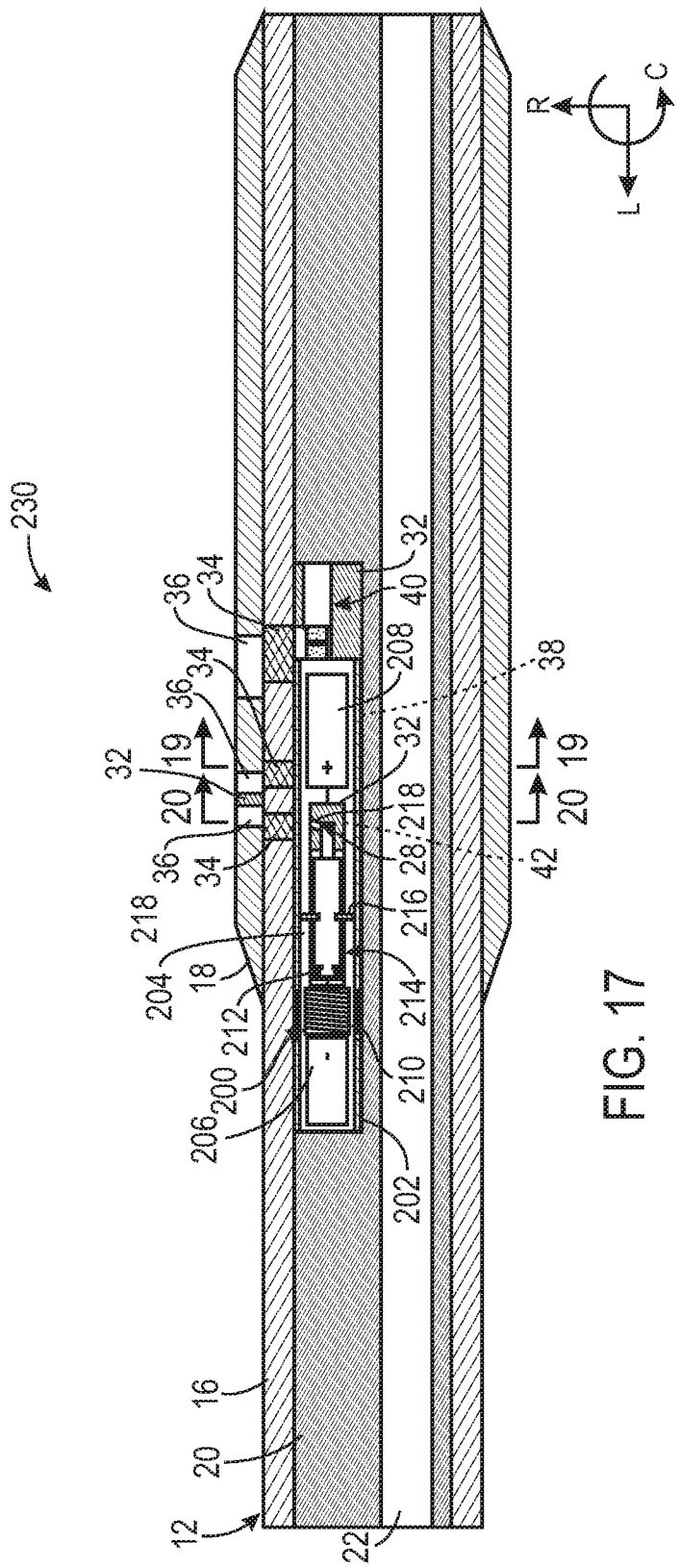
FIG. 17 is a schematic diagram of a configuration of an LWD tool employing the bipolar X-ray generator of FIG. 16, in accordance with an embodiment.

When the bipolar X-ray generator 200 is employed in the LWD tool 12, such as shown by a configuration 230 of FIG. 17, certain properties of the bipolar X-ray generator 200, namely insulation with respect to ground and size, may be considered. In the configuration 230 of FIG. 17, the LWD tool 12 includes the bipolar X-ray generator 200 installed in an annular chassis 20, though other embodiments may employ the bipolar X-ray generator 200 in a mandrel-mounted design. As can be seen in FIG. 17, the LWD tool 12 may employ less insulation with respect to ground. In addition, the bipolar X-ray generator 200 may share certain longitudinal space in the LWD tool 12 with X-ray detectors. In particular, disposed behind the bipolar X-ray generator 200 in FIG. 17 are a near X-ray detector 38 and an X-ray monitor 42.

Figure 18:
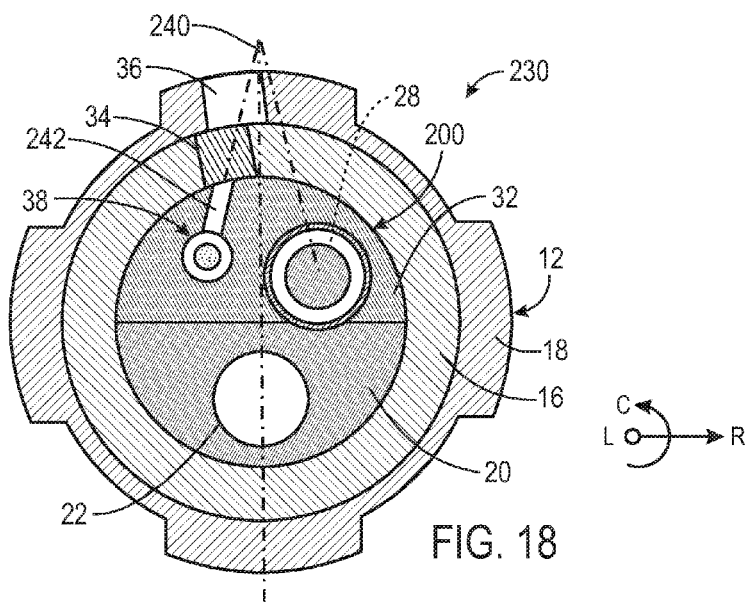
FIGS. 18 and 19 are schematic diagrams of cross-sectional views of the LWD tool configuration of FIG. 17, in accordance with embodiments.

The orientation of the near X-ray detector 38 relative to the bipolar X-ray generator 200 can be seen in FIG. 18, which presents a cross-sectional view of the configuration 230 of the LWD tool 12 at cut lines 19-19. Surrounded by shielding 32, the X-ray detector 38 may be disposed at a different circumferential location at an overlapping axial or longitudinal location with the bipolar X-ray generator 200. The X-ray detector 38 and the target 28 of the bipolar X-ray generator 200 are offset both circumferentially and longitudinally from one another as shown. Thus, when X-rays travel an X-ray path 240 to reach the near X-ray detector 38, a collimation channel 242 may be angled slightly non-orthogonally to the LWD tool 12, to account for the circumferential offset location of the near X-ray detector 38 relative to the target 28 of the bipolar X-ray generator 200. Collar windows 34 and stabilizer windows 36 may be installed to be angled accordingly.

Figure 19:
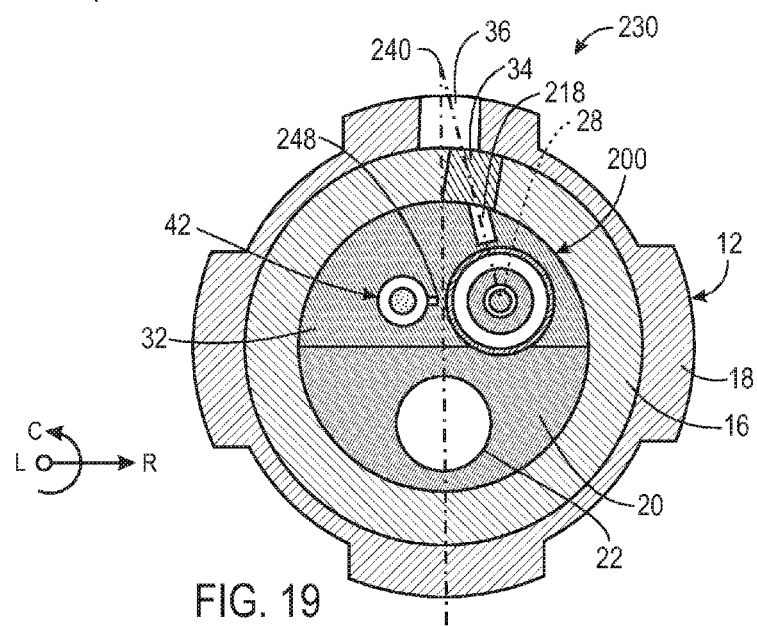

Likewise, the placement of the X-ray monitor 42 relative to the target 28 bipolar X-ray generator 200 is shown in FIG. 19, which represents a cross-sectional view of the configuration 230 of the LWD tool 12, along cut lines 20-20 of FIG. 17. As can be seen, the X-ray monitor 42 may be disposed along side the bipolar X-ray generator 200, and may monitor the output of the bipolar X-ray generator 200 through a collimation channel 248 aimed at the adjacent bipolar X-ray generator 200. Because the X-ray detector 38 may be located in a different circumferential location in the chassis 20 of the LWD tool 12 than the bipolar X-ray generator 200, the collimation channel 218 through the shielding 32 may be angled slightly non-orthogonally out of the LWD tool 12 in the direction of the X-ray detector 38, as shown in FIG. 19. In other words, the collimation channels 242 and 218 are oriented in such a way that they point to the same circumferential line along the mid-plane of the LWD tool 12. In addition, collar windows 34 and stabilizer windows 36 may be angled accordingly to allow the X-rays to be emitted from the LWD tool 12 in the non-orthogonal output angle.

Figure 20:
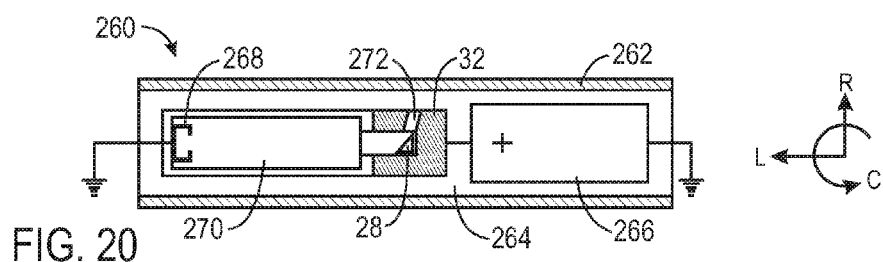
FIG. 20 is a schematic diagram of an X-ray generator having a grounded electron source, in accordance with an embodiment.

Alternatively, the LWD tool 12 may employ a grounded-electron-source X-ray generator 260, as shown in FIG. 20. Like the bipolar X-ray generator 200, the grounded-electron-source X-ray generator 260 may include a housing 262 that includes a number of components surrounded by a high voltage installation 264. A positive high voltage power supply 266 may be electrically coupled to the target 28. An electron source 268 of an X-ray tube 270 may be grounded. In operation, electrons from the electron source 268 may accelerate through the X-ray tube 270, striking the target 28 and producing X-rays through Bremsstrahlung radiation. The X-rays may be emitted through a collimation channel 218 in the grounded-electron-source X-ray generator 260.

Figure 21:
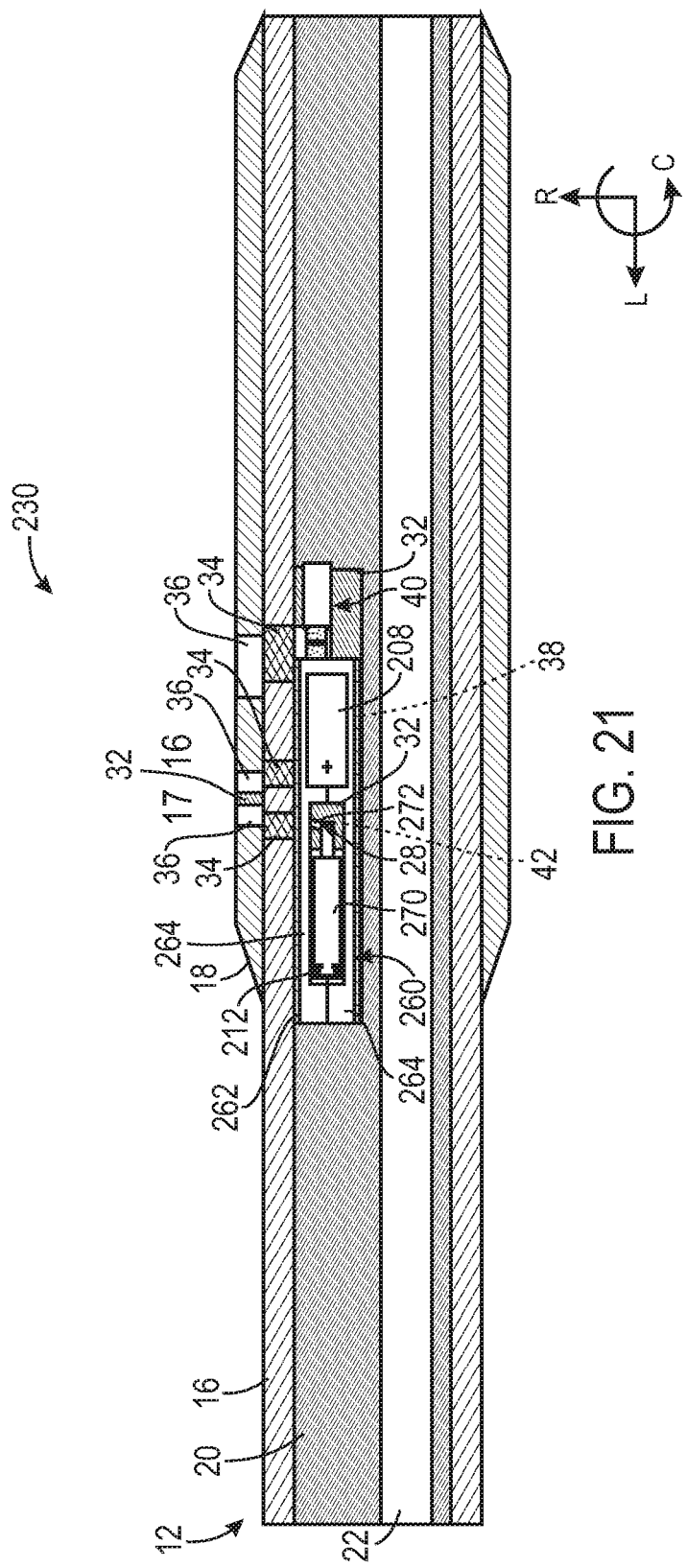
FIG. 21 is a schematic diagram of a configuration of an LWD tool employing the grounded-electron-source X-ray generator of FIG. 17, in accordance with an embodiment.

FIG. 21 presents a configuration 280 of the LWD tool 12 that employs such a grounded-electron-source X-ray generator 260. As should be appreciated, the configuration 280 affords the advantage of a simplified construction, as there may be no need to provide power to a floating cathode. Accordingly, a high voltage insulation transformer may not be needed, as in the power supply transformer 210 of the bipolar X-ray generator 200. In other respects, the configuration 280 of the LWD tool 12 may be substantially the same as the configuration to 230 of FIGS. 18-20.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A logging-while-drilling tool comprising:
    a circumferential drill collar;
    a circumferential stabilizer radially exterior to the drill collar;
    a circumferential mud channel radially interior to the circumference of the drill collar;
    a mandrel chassis radially interior to the mud channel;

a plurality of X-ray permissive mandrel supports disposed within the mud channel between the mandrel chassis and drill collar;

an electronic X-ray generator disposed within the mandrel chassis, wherein the electronic X-ray generator is configured to emit X-rays through a first collimation channel and at least one of the plurality of X-ray permissive mandrel supports to exit the logging-while-drilling tool into a subterranean formation at a first azimuthal angle; and a first X-ray detector configured to detect X-rays that return to the logging-while-drilling tool after scattering in the subterranean formation.

2. The logging-while-drilling tool of claim 1, wherein the first X-ray detector is configured to detect X-rays that return to the logging-while-drilling tool after scattering in the subterranean formation generally from the first azimuthal angle.

3. The logging-while-drilling tool of claim 1, wherein the first X-ray detector is disposed within the mandrel chassis.

4. The logging-while-drilling tool of claim 1, wherein the first X-ray detector is disposed within the drill collar or the stabilizer, or within a combination of the drill collar and the stabilizer.

5. The logging-while-drilling tool of claim 4, comprising a second collimation channel configured to permit X-rays from the electronic X-ray generator to exit the logging-while-drilling tool into the subterranean formation at a second azimuthal angle and comprising a second X-ray detector disposed within the drill collar or the stabilizer, or within the combination of the drill collar and the stabilizer, wherein the second X-ray detector is configured to detect X-rays that return to the logging-while-drilling tool after scattering in the subterranean formation generally from the second azimuthal angle.

6. The logging-while-drilling tool of claim 4, wherein the first X-ray detector is housed in a titanium pressure housing without separate X-ray permissive windows.

7. The logging-while-drilling tool of claim 1, wherein the first X-ray detector is configured to detect X-rays that pass through a first collimation channel, and comprising a third X-ray detector azimuthally adjacent to the first X-ray detector that is configured to detect X-rays through a second collimation channel.

8. The logging-while-drilling tool of claim 7, wherein the first collimation channel and the second collimation channel are substantially parallel.

9. The logging-while-drilling tool of claim 1, wherein the mandrel chassis is housed in a pressure housing that comprises titanium.

* * * * *